United States Patent [19]

Förster et al.

[11] Patent Number: 4,585,471
[45] Date of Patent: Apr. 29, 1986

[54] NOVEL SUBSTITUTED 5-TRIFLUOROMETHYL-1,3,4-THIADIAZOL-2-YL-OXY-ACETIC ACID AMIDE HERBICIDES

[75] Inventors: Heinz Förster, Wuppertal, Fed. Rep. of Germany; Wolfgang J. Hofer, deceased, late of Wuppertal, Fed. Rep. of Germany, by Erika Irene Hofer, heir; Robert R. Schmidt, Bergisch-Gladbach; Ludwig Eue, Leverkusen, both of Fed. Rep. of Germany

[73] Assignee: Bayer Aktiengesellschaft, Leverkusen, Fed. Rep. of Germany

[21] Appl. No.: 733,662

[22] Filed: May 10, 1985

Related U.S. Application Data

[63] Continuation of Ser. No. 490,900, May 5, 1983, abandoned.

[30] Foreign Application Priority Data

May 15, 1982 [DE] Fed. Rep. of Germany ....... 3218482

[51] Int. Cl.$^4$ ................... A01N 43/82; C07D 285/12; C07D 417/12
[52] U.S. Cl. ........................................... 71/90; 71/92; 71/94; 544/137; 544/367; 546/146; 546/165; 546/209
[58] Field of Search ....................... 548/129; 546/209; 544/137, 367; 71/92, 94, 90

[56] References Cited

U.S. PATENT DOCUMENTS 4,097,669 6/1978 Reisdorff et al. ................... 548/136

FOREIGN PATENT DOCUMENTS 18497 11/1980 European Pat. Off. ............ 548/129
2914003 10/1980 Fed. Rep. of Germany ...... 548/129
3004326 8/1981 Fed. Rep. of Germany .

Primary Examiner—Robert T. Bond
Attorney, Agent, or Firm—Sprung, Horn, Kramer & Woods

[57] ABSTRACT

Substituted 5-trifluoromethyl-1,3,4-thiadiazol-2-yl-oxyacetic acid amides of the formula

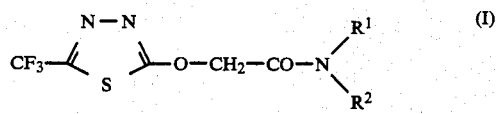

in which $R^1$ and $R^2$ are identical or different and each represent alkyl, alkenyl, alkinyl, alkoxy, aralkyl, cycloalkyl, cycloalkenyl or aryl, each of which is optionally substituted, or a nitrogen-containing heterocyclic radical, or, together with the nitrogen atom to which they are bonded, form an optionally substituted, optionally partially unsaturated and optionally benzo-fused monocyclic or bicyclic structure which optionally contains further hetero atoms, with the proviso that $R_1$ does not represent methyl when $R^2$ represents phenyl, which possess herbicidal activity.

20 Claims, No Drawings

NOVEL SUBSTITUTED 5-TRIFLUOROMETHYL-1,3,4-THIADIAZOL-2-YL-OXY-ACETIC ACID AMIDE HERBICIDES

This is a continuation, of application Ser. No. 490.900, filed May 5, 1983, now abandoned.

The invention relates to new substituted 5-trifluoromethyl-1,3,4-thiadiazol-2yl-oxyacetic acid amides, a process for their preparation and their use as herbicides.

It has already been disclosed that certain azolyloxycarboxylic acid amides can be used as herbicides (see, for example, DE-OS (German Published Specification) No. 2,914,003 and DE-OS (German Published Specification) No. 2,914,003 and DE-OS (German Published Specification) No. 3,004,326). Thus, for example, 4,5-dichloro-1,3-thiazol-2-yl-oxyacetic acid N,N-diehtylamide can be employed for selectively combating grasses in dicotyledon crops such as, for example, cotton; however, the compound is not sufficiently active against dicotyledon weeds.

New substituted 5-trifluoromethyl-1,3,4-thiadiazol-2-yl-oxyacetic acid amides of the formula

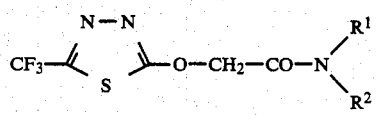

in which $R^1$ and $R^2$ are identical or different and each represent alkyl, alkenyl, alkinyl, alkoxyl, aralkyl, cycloalkyl, cycloalkenyl or aryl, each of which is optionally substituted, or a nitrogen-containing heterocyclic radical, or, together with the nitrogen atom to which they are bonded, form an optionally substituted, optionally partially unsaturated and optionally benzo-fused monocyclic or bicyclic structure which optionally contains further hetero atoms, with the proviso that $R^1$ does not represent methyl when $R^2$ represents phenyl, have been found.

The new compounds of the formula (I) are obtained when hydroxyacetic acid amides of the formula

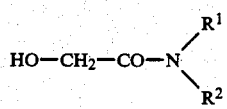

in which $R^1$ and $R^2$ have the meaning given above, are reacted with 2-chloro-5-trifluoromethyl-1,3,4-thiadiazole of the formula

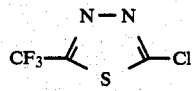

in the presence of an acid acceptor and, if appropriate, using a diluent.

The new substituted 5-trifluoromethyl-1,3,4-thiadiazol-2-yl-oxyacetic acid amides of the formula (I) are distinguished by powerful herbicidal activity.

Surprisingly, the active compounds according to the invention, of the formula (I), in addition to being very active against grasses, are also very active against dicotyledon weeds. The new active compounds thus have substantial advantages over the previously known azolyloxycarboxylic acid amides (according to DE-OS (German Published Specifications) 2,914,003 and 3,004,326), which essentially are active only against grasses.

The invention preferably relates to 5-trifluoromethyl-1,3,4-thiadiazol-2-yl-oxyacetic acid amides of the formula (I) in which $R^1$ and $R^2$, which can be idential or different, each represent alkyl, cyanoalkyl, alkoxyalkyl, alkylthioalkyl, alkenyl, alkinyl or alkoxy, each having up to 10 C atoms, cycloalkyl or cycloalkenyl, each having up to 12 C atoms, or aralkyl which has 1 or 2 carbon atoms in the alkyl part and 6 or 10 carbon atoms in the aryl part which is optionally substituted by halogen, or represents aryl which has 6 or 10 carbon atoms, it being possible for the aryl radical to be substituted by 1 to 3 halogen atoms, 1 to 3 alkyl groups each having 1 to 4 carbon atoms, nitro, cyano or alkoxy having 1 to 4 carbon atoms, or wherein the radicals $R^1$ and $R^2$, together with the nitrogen atom to which they are bonded, form an optionally partially unsaturated and/or benzo-fused monocyclic or bicyclic structure which has up to 15 carbon atoms and is optionally substituted by 1 to 3 alkyl groups, each having 1 to 5 carbon atoms, or wherein the radicals $R^1$ and $R^2$, together with the nitrogen atom to which they are bonded, form a saturated monocyclic structure which has up to 5 carbon atoms, contains a further nitrogen atom, oxygen atom or sulphur atom, and is optionally substituted by 1 to 3 alkyl groups, each having 1 to 5 carbon atoms, with the proviso that $R^1$ does not represent methyl when $R^2$ represents phenyl.

The invention relates, in particular, to compounds of the formula (I) in which $R^1$ represents $C_1$–$C_5$-alkyl, cyanoethyl, $C_1$–$C_4$-alkoxy-ethyl, allyl, propargyl, 1-methyl-propargyl or 1,1-dimethyl-propargyl, and $R^2$ represents $C_1$–$C_5$-alkyl, $C_1$–$C_5$-alkoxy, cyanoethyl, $C_1$–$C_4$-alkoxy-ethyl, allyl, propargyl, 1-methyl-propargyl, 1,1-dimethylpropargyl, cyclopentyl, cyclohexyl, 3,4,6-trimethyl-cyclohexen-1-yl, benzyl, naphthyl or phenyl which is optionally substituted by 1 to 3 radicals (methyl, chlorine, fluorine, trifluoromethyl, methoxy, methylthio, trifluoromethoxy and/or trifluoromethylthio), or wherein the radicals $R^1$ and $R^2$, together with the nitrogen atom to which they are bonded, represent pyrrolidyl, monoalkyl- or dialkyl-pyrrolidyl having 1 to 3 carbon atoms per alkyl group, morpholinyl or dialkylmorpholinyl having 1 to 3 carbon atoms per alkyl group, piperidyl, monoalkyl-, dialkyl- or trialkylpiperidyl having 1 to 3 carbon atoms per alkyl group, perhydroazepinyl (hexamethyleneimino radical), the heptamethyleneimino radical, 1,2,3,4-tetrahydroindolyl, moinoalkyl- or dialkyl tetrahydroindolyl having up to 3 carbon atoms per alkyl group, perhydroindolyl, monalkyl- or dialkylperhydroindolyl having 1 to 3 carbon atoms per alkyl group, 1,2,3,4-tetrahydroquinolyl or 1,2,3,4-tetrahydro-iso-quinolyl, monoalkyl- or dialkyl-1,2,3,4-tetrahydroquinolyl or -isoquinolyl having 1 to 3 carbon atoms per alkyl group, perhydroquinolyl or perhydro-iso-quinolyl, monoalkylor dialkyl-perhydroquinolyl or -perhydroisoquinolyl having 1 to 3 carbon atoms per alkyl group, perhydrothiazolyl, perhydrooxazolyl, perhydrooxazinyl or the radical

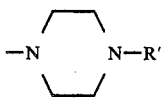

wherein

R' represents $C_1$-$C_4$-alkyl, or phenyl which is optionally substituted by $C_1$-$C_2$-alkyl, $C_1$-$C_2$-alkoxy, fluorine, chlorine, bromine, trifluoromethyl and/or nitro—once again with the proviso that $R^1$ does not represent methyl when $R^2$ represents phenyl.

If 2-chloro-5-trifluoromethyl-1,3,4-thiadiazole and, for example, hydroxyacetic acid 2-ethylpiperidide are used as starting materials, the course of the reaction in the process according to the invention can be represented by the following equation

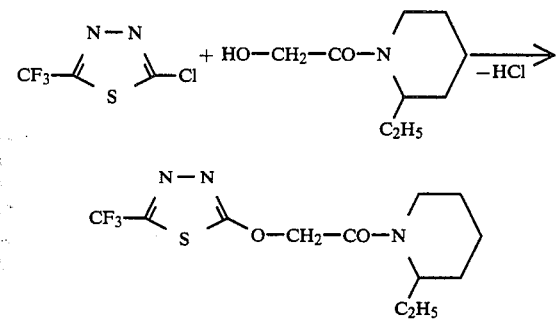

Formula (II) gives a definition of the hydroxyacetic acid amides to be used as starting materials. In this formula, $R^1$ and $R^2$ preferably or particularly represent those radicals which have already been mentioned within the scope of the substituent definitions of formula (I) as being preferred or particularly preferred, respectively.

The following may be mentioned as examples of starting materials of the formula (II): hydroxyacetic acid dimethylamide, diethylamide, di-n-propylamide, di-iso-propylamide, N-methyl-N-iso-propylamide, N-methyl-N-isobutylamide, N-methyl-N-sec.-butylamide, N-propyl-N-sec.-butylamide, N-methyl-N-(2-cyanoethyl)-amide, di-(2-methoxyethyl)-amide, di-allyl-amide, N-methyl-N-propargyl amide, N-methyl-N-(1-methyl-propargyl)-amide, dipropargylamide, N-methyl-N-cyclopentyl-amide, N-methyl-N-cyclohexylamide, N-methyl-N-(2-nitro-phenyl)-, N-methyl-N-(3-nitro-phenyl)- and N-methyl-N-(4-nitro-phenyl)-amide, N-methyl-N-(2-chloro-phenyl)-, N-methyl-N-(3-chloro-phenyl)- and N-methyl-N-(4-chloro-phenyl)-amide, N-methyl-N-(3-nitro-6-methylphenyl)-amide, N-ethyl-anilide, N-ethyl-N-(2-nitrophenyl)-, N-ethyl-(3-nitro-phenyl)- and N-ethyl-N-(4-nitro-phenyl)-amide, N-ethyl-N-(2-chloro-phenyl)-, N-ethyl-N-(3-chloro-phenyl)- and N-ethyl-N-(4-chlorophenyl)-amide, N-ethyl-N-(3-nitro-6methyl-phenyl)-amide, N-propyl-anilide, N-propyl-N-(2-nitro-phenyl)-, N-propyl-N-(3-nitro-phenyl)- and N-propyl-N-(4-nitro-phenyl)-amide, N-propyl-N-(2-chloro-phenyl)-, N-propyl-N-(3-chloro-phenyl)- and N-propyl-N-(4-chloro-phenyl)-amide, N-propyl-N-(2-methyl-phenyl)-, N-propyl-N-(3-methylphenyl)- and N-propyl-N-(4-methyl-phenyl)-amide, N-propyl-N-(3-nitro-6methyl-phenyl)-amide, N-butylanilide, N-methyl-N-naphth-1-ylamide, N-methyl-N-naphth-2-ylamide, N-ethyl-N-naphth-1ylamide, N-ethyl-N-napth-2-ylamide, N-methyl-N-benzylamide, N-ethyl-N-benzylamide, N-propyl-N-benzylamide, N-butyl-N-benzylamide, pyrrolidide, 1-methyl-pyrrolidide, morpholide, piperidide, 2-methyl-piperidide, 2-methyl-piperidide, 4-methylpiperidide, 2,4-dimethyl-piperidide, 3,5-dimethylpiperidide, 3,5-diethylpiperidide, 2,4,6-trimethylpiperidide, 2-ethyl-piperidide, 4-ethyl-piperidide, 2,4-diethyl-piperidide, 2,4,6-triethyl-piperidide, 2-methyl-4-ethyl-piperidide, 2-ethyl-4-methyl-piperidide, 2-methyl-5-ethyl-piperidide, 2-ethyl-5-methyl-piperidide, 2-methyl-6ethyl-piperidide, 1,2,3,4-tetrahydroindolide, 2-methyl-1,2,3,4-tetrahydroindolide, perhydroindolide, 2-methyl-perhydroindolide, 2,2-dimethyl-perhydroindolide, 2-methyl-1,2,3,4-tetrahydroquinolide, perhydroquinolide, 2-methyl-perhydroquinolide, 1,2,3,4-tetrahydro-isoquinolide and perhydroisoquinolide; and also N-methyl-N-(2-methylthio-phenyl)-, N-methyl-N-(3-methylthiophenyl)- and N-methyl-N-(4-methylthio-phenyl)-amide; N-methyl-N-(2fluorophenyl)-, N-methyl-N-(3-fluorophenyl- and N-methyl-N-(4-fluorophenyl)-amide; N-methyl-N-( 2-trifluoro-methylphenyl)-, N-methyl-N-(3-trifluoromethylphenyl)- and N-methyl-N-(4trifluoromethylphenyl)amide; N-methyl-N-(2trifluoromethoxyphenyl)-, N-methyl-N-(3-trifluoromethoxyphenyl)- and N-methyl-N-(4-trifluoromethoxyphenyl)-amide; and N-methyl-N-(2-(2,2,2-trifluoroethyl)phenyl)-amide.

Hydroxy-carboxylic acid amides of the formula (II) are known (see U.S. Pat. No. 3,399,988; and De-OS (German Published Specifications) Nos. 2,201,432 and 2,647,481). As shown in the equation below, they can be prepared using chloroacetyl chloride as a starting material:

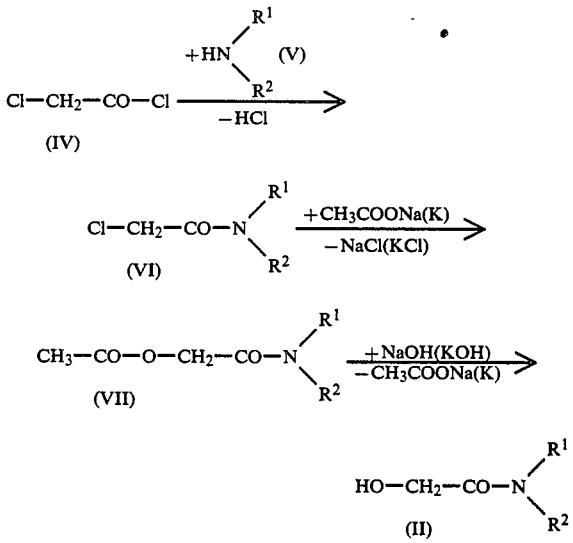

For this purpose, the chloroacetyl chloride, of the formula (IV), which is known from the literature, is first converted into the corresponding chloroacetic acid amides of the formula (VI), using amines of the formula (V)—wherein $R^1$ and $R^2$ have the meaning given above—if appropriate in the presence of an acid-binding agent, such as, for example, triethylamine and if appropriate using an inert diluent, such as, for example, 1,2-dichloroethane, at temperatures between −20° and 100° C., preferably between −10° and 50° C. These products are worked up according to customary methods, by washing with water, drying the organic phase and distilling off the solvent.

The compounds of the formula (VI) are reacted with sodium acetate or potassium acetate, if appropriate using a diluent, such as, for example, acetic acid or dimethylsulphoxide, at temperatures between 20° and 150° C., preferably between 50° and 120° C., to give the corresponding acetoxy-acetic acid amides of the formula (VII). Where the products obtained in this reaction are in crystalline form, they are isolated by filtering them off under suction. Otherwise, working-up is carried out by customary methods, for example by distilling off the solvent in vacuo, taking up the residue in methylene chloride, washing the solution with water and distilling off the solvent.

By reaction with aqueous-alcoholic sodium hydroxide solution or potassium hydroxide solution at temperatures between 0° and 100° C., preferably between 10° and 50° C., the compounds of the formula (VII) can be deacylated to give the compounds of the formula (II). To isolate the products, the solvents are distilled off in vacuo, the residue is extracted with an organic solvent such as, for example, methylene chloride or ethyl acetate, the solution is dried and the solvent is distilled off.

Formula (III) gives a definition of the 2-chloro-5-trifluoromethyl-1,3,4-thiadiazole to be used as a starting material. This compound is known from the literature (see J. Heterocyclic Chem. 1974, volume 11(3), pages 343–345; it can be prepared, for example, by a process in which the corresponding 2-amino compound is dissolved with hydrochloric acid in water and the solution is reacted with sodium nitrite, while cooling with ice, the mixture is stirred for several hours at temperatures between −10° and +50° C., the reaction product is extracted with toluene and, after the organic phase has been washed and dried, is worked up by distillation.

The process for the preparation of the new compounds of the formula (I) is preferably carried out using suitable solvents or diluents. Virtually all inert organic solvents are suitable for this purpose. These include, in particular, alcohols, such as methanol, ethanol n- and iso-propanol, and n-, iso-, sec.- and tert.-butanol, ethers, such as diethyl ether, dibutyl ether, tetrahydrofuran, diglyme and dioxane, ketones, such as acetone, methyl ethyl ketone, methyl isopropyl ketone and methyl isobutyl ketone, nitriles, such as acetonitrile and propionitrile, and the highly polar solvents dimethylformamide, dimethylsulphoxide, sulpholane and hexamethylphosphoric acid triamide.

Virtually all customarily usable acid-binding agents can be employed as acid acceptors: these include, in particular, alkali metal hydroxides, alkaline earth metal hydroxides, alkali metal oxides and alkaline earth metal oxides, such as sodium hydroxide, potassium hydroxide and in particular lithium hydroxide, and calcium oxide or calcium hydroxide, alkali metal carbonates and alkaline earth metal carbonates, such as sodium carbonate, potassium carbonate and calcium carbonate, alkali metal alcoholates, such as sodium methylate, sodium ethylate and sodium tert.-butylate, potassium methylate, potassium ethylate and potassium tert.-butylate, and also aliphatic, aromatic or heterocyclic amines, such as triethylamine, dimethylaniline, dimethylbenzylamine, pyridine, diazabicyclooctane and diazabicycloundecene.

The reaction temperature can be varied within a relatively wide range. In general, the reaction is carried out at between −50° and +150° C., preferably at −20° to +100° C.

The process according to the invention is carried out in general under atmospheric pressure.

In carrying out the process according to the invention, 1.0 to 1.5 mols of hydroxyacetic acid amide of the formula (II) are employed per mol of 2-chloro-5-trifluoromethyl-1,3,4-thiadiazole of the formula (III). The reaction is carried out in general in a suitable diluent, and the reaction mixture is stirred at the required temperature for several hours.

The products are isolated according to customary methods: if appropriate, a part of the diluent is distilled off under reduced pressure, and the remainder of the reaction mixture is poured into water. If, in this process, the products are obtained in crystalline form, they are isolated by filtering them off under suction. Otherwise, the organic products are extracted with a water-immiscible solvent, such as, for example, toluene or methylene chloride; after the solution has been washed and dried, the solvent is then distilled off in vacuo from the organic phase. The products which remain are characterized by their melting point or their refractive index.

The active compounds according to the invention can be used as defoliants, desiccants, agents for destroying broad-leaved plants and especially as weedkillers. By weeds, in the broadest sense, there are to be understood all plants which grow in locations where they are undersired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Spheoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention also show, in addition to a very good action against monocotyledon weeds, a good herbicidal action against dicotyledon weeds, The active compounds according to the invention can be employed selectively in various cultures, especially in dicotyledon crops and in rice and cereals.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cychohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthyalocyanine dyestuffs, and trace nutrients such as salts or iron, manganese, boron, cooper, cobalt, molybdenum and zinc.

The formulations in general contain between 0.1 and 95% by weight of active compound, preferably between 0.5 and 90%.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.1 and 10 kg of active compound per ha, preferably between 0.1 and 5 kg/ha.

The examples which follow serve to illustrate the invention further.

PREPARATION EXAMPLES

EXAMPLE 1

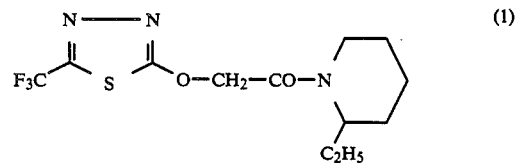

4.3 g (0.025 mol) of hydroxyacetic acid 2-ethylpiperidide and 4.7 g (0.025 mol) of 2-chloro-5-trifluoromethyl-1,3,4-thiadiazole are added successively to a solution of 2.8 g (0.025 mol) of potassium tert.-butanolate in 50 ml of tert.-butanol, at a temperature between 20° and 30° C. The reaction mixture is stirred for 3 hours, then diluted with 100 ml of methylene chloride, washed with 50 ml of 2N hydrochloric acid and then with 50 ml of water, dried, and freed from solvent by concentration in the vacuum from a water jet.

5.0 g (66% of theory) of (5-trifluoromethyl-1,3,4-thiadiazol-2-yl-oxy)-acetic acid 2-ethylpiperidide are obtained as an oil refractive index $n_D^{19} = 1.4954$.

EXAMPLE 2

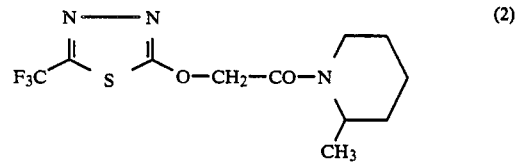

A solution of 2.4 g (0.06 mol) of sodium hydroxide in 5 ml of water is added dropwise to a solution, cooled to −20° C., of 12.0 (0.06 mol) of 2-chloro-5-trifluoromethyl-1,3,4-thiadiazol and 10.0 g of hydroxyacetic acid 2-methylpiperidide in 100 ml of toluene.

The reaction mixture is stirred for 2 hours at −20° C., poured into 100 ml or water and acidified with 2N hydrochloric acid. The organic phase is separated off, washed with water, dried, and freed from solvent by concentration in the vaccumm from a water jet.

10.0 g(54% of theory) of (5-trifluoromethyl-1,3,4-thiadiazol-2-yl-oxy)-acetic acid 2-methylpiperidide are obtained as an oil of refractive index $n_d^{20}=1.4934$.

The compounds of the formula (I) which are listed in the table below can be prepared analogously to Examples 1 and 2:

TABLE 1

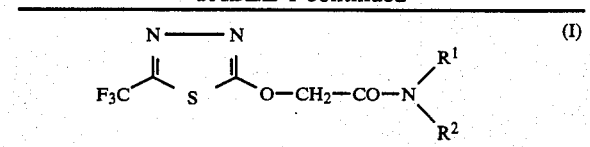

Examples of compounds of the formula (I)

| Compound No. | $-N{<}^{R^1}_{R^2}$ | Melting point or refractive index |
|---|---|---|
| 3 | 4-methylpiperidin-1-yl | 126° C. |
| 4 | N(CH$_3$)(3-CF$_3$-C$_6$H$_4$) | 55° C. |
| 5 | −N(C$_2$H$_5$)$_2$ | 58–60° C. |
| 6 | 3,5-dimethylpiperidin-1-yl | $n_D^{19} = 1.4932$ |
| 7 | 4-ethylpiperidin-1-yl | $n_D^{19} = 1.4945$ |
| 8 | −N(C$_2$H$_5$)−CH(CH$_3$)$_2$ | $n_D^{19} = 1.4689$ |
| 9 | decahydroquinolin-1-yl | $n_D^{19} = 1.5065$ |
| 10 | 2,4,6-trimethylpiperidin-1-yl | $n_D^{19} = 1.4905$ |

TABLE 1-continued

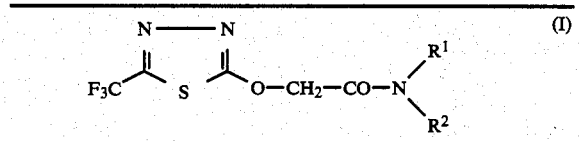

Examples of compounds of the formula (I)

| Compound No. | $-N{<}^{R^1}_{R^2}$ | Melting point or refractive index |
|---|---|---|
| 11 | 1,2,3,4-tetrahydroquinolin-1-yl | $n_D^{19} = 1.5584$ / 60° C. |
| 12 | 3-ethylpiperidin-1-yl | $n_D^{20} = 1.4869$ |
| 13 | 3-methylpiperidin-1-yl | $n_D^{20} = 1.4860$ |
| 14 | hexamethyleneimin-1-yl (azepan-1-yl) | $n_D^{20} = 1.4901$ |
| 15 | N(CH$_3$)(2-CH$_3$-C$_6$H$_4$) | 67° C. |
| 16 | N(CH$_3$)(4-CH$_3$-2-NO$_2$-C$_6$H$_3$) | 110° C. |
| 17 | 3,5-dimethylpiperidin-1-yl | 56° C. |
| 18 | N(CH$_3$)(3-CH$_3$-C$_6$H$_4$) | 63° C. |

TABLE 1-continued

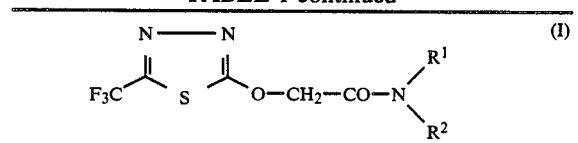

Examples of compounds of the formula (I)

| Compound No. | $-N\begin{smallmatrix}R^1\\R^2\end{smallmatrix}$ | Melting point or refractive index |
|---|---|---|
| 19 | —N(C₂H₅)(3-CH₃-C₆H₄) | 50° C. |
| 20 | —N(C₂H₅)(C₆H₅) | 76° C. |
| 21 | —N(CH₃)(3-Cl-C₆H₄) | $n_D^{20} = 1.5260$ |
| 22 | —N(CH₃)—C₄H₉ | $n_D^{20} = 1.4678$ |
| 23 | —N(OCH₃)—CH(CH₃)CH₂CH₃ | $n_D^{20} = 1.4615$ |
| 24 | —N(CH₃)(3-NO₂-C₆H₄) | $n_D^{20} = 1.5371$ |
| 25 | —N(CH₂CH₂CH₃)₂ | $n_D^{20} = 1.4672$ |
| 26 | —N(CH₃)—CH₂—C₆H₅ | $n_D^{20} = 1.5200$ |
| 27 | —N(CH₃)(3-CH₃-4-Cl-C₆H₃) | |
| 28 | —N(CH₃)(3,4-Cl₂-C₆H₃) | |
| 29 | —N(CH₃)(2,4-Cl₂-C₆H₃) | |

TABLE 1-continued

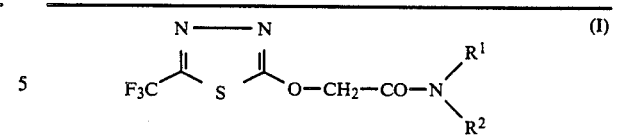

Examples of compounds of the formula (I)

| Compound No. | $-N\begin{smallmatrix}R^1\\R^2\end{smallmatrix}$ | Melting point or refractive index |
|---|---|---|
| 30 | —N(CH₃)(2-SCF₃-C₆H₄) | |
| 31 | —N(CH₃)(4-SCF₃-C₆H₄) | |
| 32 | —N(CH₃)(3-SCF₃-C₆H₄) | |
| 33 | —N(C₄H₉)₂ | |
| 34 | —N(CH₃)—CH₂OCH₃ | |
| 35 | —N(C₂H₅)—CH₂CF₃ | |
| 36 | —N(CH₃)(3,3,5-trimethyl-cyclohex-1-enyl) | |
| 37 | —N(CH(CH₃)₂)(C₆H₅) | |
| 38 | —N(C₃H₇-n)(C₆H₅) | |
| 39 | —N(CH₃)(2,3-(CH₃)₂-C₆H₃) | |

The 2-chloro-5-trifluoromethyl-1,3,4-thiadiazole to be employed as a starting compound can be prepared as follows:

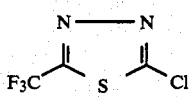 (III)

A mixture of 126 g (0.75 mol) of 2-amino-5-trifluoromethyl-1,3,4-thiadiazole, 17.9 g (0.28 mol) of copper powder and 1.5 liters of concentrated hydrochloric acid is cooled to −10° C., and a solution of 207 g (3 mols) of sodium nitrite in 300 ml of water is added dropwise. The mixture is stirred for one hour at 0° C., and heated at 40° to 50° C. for one hour. It is extracted with 500 ml of methylene chloride, the organic solution is washed with twice 300 ml of water, dried over sodium sulphate and filtered, the solvent is distilled off under atmospheric pressure and the residue is distilled in the vacuum from a water jet.

90 g (64% of theory) of 2-chloro-5-trifluoromethyl-1,3,4-thiadiazole of boiling point 46° C. (16 mbar) are obtained.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control
100%=total destruction

In this test, for example, the following compounds according to the Preparation Examples show an excellent activity: 1, 2, 5, 15, 18.

It is understood that the specification and examples are illustrative but not limitative of the present invention and that other embodiments within the spirit and scope of the invention will suggest themselves to those skilled in the art.

We claim:

1. A sustituted 5-trifluoromethyl-1,3,4-thiadiazol-2-yl-ocyacetic acid amide of the formula

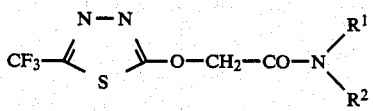

in which $R^1$ is $C_1$-$C_5$-alkyl, or allyl, and
$R^2$ is $C_1$-$C_5$-alkyl, allyl, or phenyl which is optionally substituted by up to 3 methyl, chlorine, fluorine, trifluoromethyl and/or methoxy radicals or
$R^1$ and $R^2$, together with the nitrogen atom to which they are bonded, form a 1,2,3,4-tetrahydro-quinolyl radical with the proviso that $R^1$ is not methyl when $R^2$ is phenyl.

2. A compound according to claim 1, wherein such compound is (5-trifluoromethyl-1,3,4-thiadiazol-2-yl-oxy)acetic acid 2-methylpiperidide of the formula

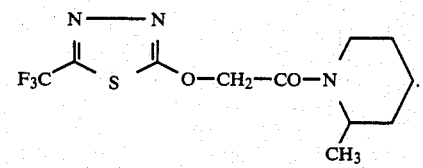

3. A compound according to claim 1, wherein such compound is (5-trifluoromethyl-1,3,4-thiadiazol-2-yl-oxy)acetic acid 2-ethylpiperidide of the formula

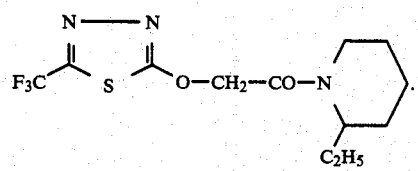

4. A compound according to claim 1, wherein such compound is (5-trifluoromethyl-1,3,4-thiadiazol-2-yl-oxy)acetic acid N-methyl-N-(2-methyl-phenyl)-amide of the formula

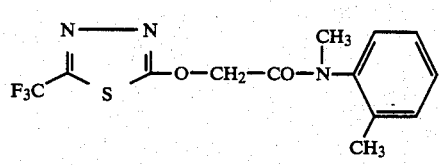

5. A compound according to claim 1, wherein such compound is (5-trifluoromethyl-1,3,4-thiadiazol-2-yl-oxy)acetic acid N-methyl-N-(3-methyl-phenyl)-amide of the formula

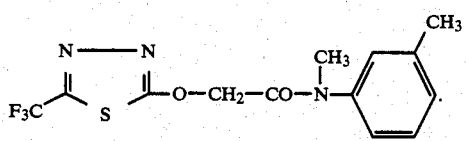

6. A compound according to claim 1, wherein such compound is (5-trifluoromethyl-1,3,4-thiadiazol-2-yl-oxy)acetic acid N,N-diethylamide of the formula

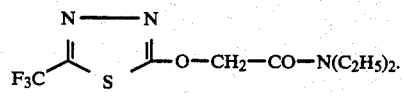

7. A herbicidal composition comprising a herbicidally effective amount of a compound according to claim 1 and a diluent.

8. A compound according to claim 1, wherein said compound has the formula

9. A compound according to claim 1, wherein said compound has the formula

[structure: 5-CF3-1,3,4-thiadiazol-2-yl-O-CH2-C(O)-N(C2H5)-(3-methylphenyl)]

10. A compound according to claim 1, wherein said compound has the formula

[structure: 5-CF3-1,3,4-thiadiazol-2-yl-O-CH2-C(O)-N(C2H5)-phenyl]

11. A compound according to claim 1, wherein said compound has the formula

[structure: 5-CF3-1,3,4-thiadiazol-2-yl-O-CH2-C(O)-N(CH3)-(3-chlorophenyl)]

12. A compound according to claim 1, wherein said compound has the formula

[structure: 5-CF3-1,3,4-thiadiazol-2-yl-O-CH2-C(O)-N(CH3)-(3-nitrophenyl)]

13. A compound according to claim 1, wherein said compound has the formula

[structure: 5-CF3-1,3,4-thiadiazol-2-yl-O-CH2-C(O)-N(C3H7-n)2]

14. A compound according to claim 1, wherein the compound has the formula

[structure: 5-CF3-1,3,4-thiadiazol-2-yl-O-CH2-C(O)-N(CH3)-(3-trifluoromethylphenyl)]

15. A compound according to claim 1, wherein the compound has the formula

[structure: 5-CF3-1,3,4-thiadiazol-2-yl-O-CH2-C(O)-N(C2H5)2]

16. A compound according to claim 1, wherein the compound has the formula

[structure: 5-CF3-1,3,4-thiadiazol-2-yl-O-CH2-C(O)-N(1,2,3,4-tetrahydroquinolinyl)]

17. A compound according to claim 1, wherein the compound has the formula

[structure: 5-CF3-1,3,4-thiadiazol-2-yl-O-CH2-C(O)-N(3-methylpiperidinyl)]

18. A compound according to claim 1, wherein the compound has the formula

[structure: 5-CF3-1,3,4-thiadiazol-2-yl-O-CH2-C(O)-N(hexamethyleneimino)]

18. A method of combating unwanted vegetation which comprises applying to such vegetation or to a plot in which such vegetation is to be grown a herbicidally effective amount of a compound according to claim 1.

19. A method according to claim 18, wherein said compound is selected from the group consisting of

[structure: 5-CF3-1,3,4-thiadiazol-2-yl-O-CH2-C(O)-N(C2H5)-(3-methylphenyl)],

[structure: 5-CF3-1,3,4-thiadiazol-2-yl-O-CH2-C(O)-N(C2H5)-phenyl],

[structure: 5-CF3-1,3,4-thiadiazol-2-yl-O-CH2-C(O)-N(CH3)-(3-chlorophenyl)],

[structure: 5-CF3-1,3,4-thiadiazol-2-yl-O-CH2-C(O)-N(CH3)-(3-nitrophenyl)],

[structure: 5-CF3-1,3,4-thiadiazol-2-yl-O-CH2-C(O)-N(C3H7-n)2],

-continued

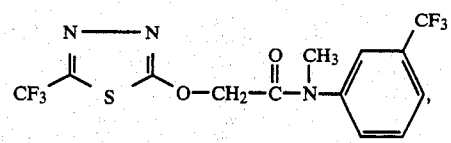

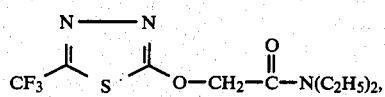

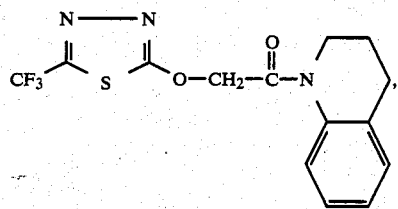

-continued

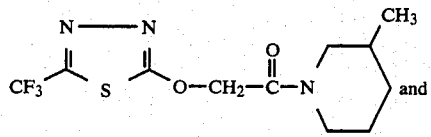

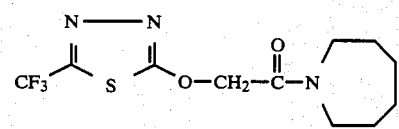

20. The method according to claim 18, wherein such compound is
(5-trifluoromethyl-1,3,4-thiadiazol-2-yl-oxy)acetic acid 2-methylpiperidide,
(5-trifluoromethyl-1,3,4-thiadiazol-2-yl-oxy)1 acetic acid 2-ethylpiperidide,
(5-trifluoromethyl-1,3,4-thiadiazol-2-yl-oxy)acetic acid N-methyl-N-(2-methyl-phenyl)-amide,
(5-trifluoromethyl-1,3,4-thiadiazol-2-yl-oxy)acetic acid N-methyl-N-(3-methyl-phenyl)-amide or
(5-trifluoromethyl-1,3,4-thiadiazol-2-yl-oxy)acetic acid N,N-diethylamide.

* * * * *

UNITED STATES PATENT AND TRADEMARK OFFICE
CERTIFICATE OF CORRECTION

PATENT NO. : 4,585,471

DATED : April 29, 1986

INVENTOR(S) : Heinz Forster, et al.

Page 1 of 2

It is certified that error appears in the above-identified patent and that said Letters Patent is hereby corrected as shown below:

| | |
|---|---|
| Title Page, under "Related U.S. Application Data" and Col. 1, line 7 | Delete "May 5, 1983" and substitute --May 2, 1983-- |
| Col. 1, line 9 | After "-2" insert -- - -- |
| Col. 1, line 18, 19 | Correct spelling of "diethylamide" |
| Col. 1, line 32 | Delete "alkoxyl" and substitute --alkoxy-- |
| Col. 2, line 8 | Correct spelling of --identical-- |
| Col. 2, line 61 | After "dialkyl" insert -- - -- |
| Col. 3, line 45 | Delete "hydroxyacetic" and substitute --Hydroxyacetic-- |
| Col. 3, line 63 and Col. 4, line 2 | After "6" insert -- - -- |
| Col. 4, line 4 | After "1" insert -- - -- |
| Col. 4, line 5 | Correct spelling of --naphth-- |
| Col. 4, line 16 | After "6" insert -- - -- |
| Col. 4, line 25 | After "N-(2" insert -- - -- |
| Col. 4, line 28 and Col. 4, line 29 | After "N-(4" insert -- - -- After "N-(2" insert -- - -- |
| Col. 7, line 33 | Delete "cychohexane" and substitute --cyclohexane-- |
| Col. 7, line 66 | Correct spelling of "phthalocyanine" |
| Col. 9, line 5 | Delete "or" and substitute --of-- |
| Col. 9, line 8 | Correct spelling of --vacuum-- |
| Col. 9, line 11 | Delete "$n_d$" and substitute --$n_D$-- |

UNITED STATES PATENT AND TRADEMARK OFFICE
CERTIFICATE OF CORRECTION

PATENT NO. : 4,585,471
DATED : April 29, 1986
INVENTOR(S) : Heinz Förster, et al.

Page 2 of 2

It is certified that error appears in the above-identified patent and that said Letters Patent is hereby corrected as shown below:

Col. 14, line 1            After "radical" insert --piperidyl, monoalkyl-, dialkyl- --piperidyl having 1 to 3 carbon atoms per alkyl group, hexamethyleneimino radical,--

Signed and Sealed this

Eleventh Day of November, 1986

Attest:

DONALD J. QUIGG

Attesting Officer         Commissioner of Patents and Trademarks